US008030548B2

(12) United States Patent
Sodhi et al.

(10) Patent No.: US 8,030,548 B2
(45) Date of Patent: Oct. 4, 2011

(54) **CYTOPLASMIC MALE STERILITY SYSTEM FOR *BRASSICA* SPECIES AND ITS USE FOR HYBRID SEED PRODUCTION IN INDIAN OILSEED MUSTARD *BRASSICA JUNCEA***

(75) Inventors: Yashpal Singh Sodhi, New Delhi (IN); Akshay Kumar Pradhan, New Delhi (IN); Vibha Gupta, New Delhi (IN); Neelakantan Arumugam, New Delhi (IN); Jagdish Kumar Verma, New Delhi (IN); Arundhati Mukhopadhyay, New Delhi (IN); Deepak Pental, New Delhi (IN)

(73) Assignees: Dhara Vegetable Oil and Foods Company Limited, Gujarat (IN); University of Delhi, New Delhi (IN)

( * ) Notice: Subject to any disclaimer, the term of this patent is extended or adjusted under 35 U.S.C. 154(b) by 934 days.

(21) Appl. No.: 11/660,510

(22) PCT Filed: Aug. 22, 2005

(86) PCT No.: PCT/IN2005/000278
§ 371 (c)(1),
(2), (4) Date: Dec. 10, 2007

(87) PCT Pub. No.: WO2006/021972
PCT Pub. Date: Mar. 2, 2006

(65) Prior Publication Data
US 2008/0148429 A1 Jun. 19, 2008

(30) Foreign Application Priority Data
Aug. 26, 2004 (IN) .......................... 1610/DEL/2004

(51) Int. Cl.
*A01H 5/00* (2006.01)
*A01H 1/02* (2006.01)
*C12N 5/04* (2006.01)
(52) U.S. Cl. ........ 800/303; 800/299; 800/306; 800/269; 435/410
(58) Field of Classification Search ........................ None
See application file for complete search history.

(56) References Cited

U.S. PATENT DOCUMENTS
6,046,383 A 4/2000 Elsenga-Boersma et al.

FOREIGN PATENT DOCUMENTS
| GB | 2 281 568 A | 3/1995 |
| WO | WO 96/21010 | 7/1996 |
| WO | WO 01/22804 A1 | 4/2001 |
| WO | WO 01/22805 A1 | 4/2001 |

OTHER PUBLICATIONS

Rajcan et al. Euphytica 123(3): 401-409 (Feb. 2002).*

Verma, J.K. et al., "Identification of stable maintainer and fertility restorer lines for 'Polima' CMS in *Brassica campestris*," Plant Breeding, vol. 119, No. 1, pp. 90-92, Feb. 2000.
Sodhi, Y.S. et al., "Identification of a Stable Maintainer Line for 'Polima' Cytoplasmic Male Sterility in Rapeseed (*B. napus* L.)," Plant Breeding, vol. 110, No. 4, pp. 334-337, 1993.
Banga, S.S., "Chapter 3: Heterosis and its Ulitilization," Breeding Oilseed Brassicas (Eds. Kuldeep S. Labana et al), Narosa Publishing House: New Delhi, pp. 21-43, 1992.
Pradhan, Akshay K. et al., "Heterosis breeding Indian mustard (*Brassica juncea* L. Czern & Coss): Analysis of component characters contributing to heterosis for yield," Euphytica, vol. 69, pp. 219-229, 1993.
Dewey, R.E. et al., "A mitochondrial protein associated with cytoplasmic male sterility in the T cytoplasm of maize," Proc. Natl. Acad. Sci. USA, vol. 84, pp. 5374-5378, Aug. 1987.
Krishnasamy, Subbiah et al., "Characterization of the radish mitochondrial *orfB* locus: possible relationship with male sterility in Ogura radish," Current Genetics, vol. 24, pp. 156-163, 1993.
Bonhomme, Sandrine et al., "Sequence and transcript analysis of the Nco2.5 Ogura-specific fragment correlated with cytoplasmic male sterility in *Brassica* cybrids," Mol Gen Genet, vol. 235, 340-348, 1992.
Janska, Hanna et al., "Stoichiometric Shifts in the Common Bean Mitochondrial Genome Leading to Male Sterility and Spontaneous Reversion to Fertility," The Plant Cell, vol. 10, pp. 1163-1180, Jul. 1998.
Vitart, V. et al., "Amplification of substoichiometric recombinant mitochondrial DNA sequences in a nuclear, male sterile mutant regenerated from protoplast culture in *Nicotiana sylvestris*," Mol Gen Genet, vol. 233, pp. 193-200, 1992.
Kanazawa, Akira et al., "Reversible Changes in the Composition of the Population of mtDNAs During Dedifferentation and Regeneration in Tobacco," Genetics, vol. 138, pp. 865-870, Nov. 1994.
Duvick, Donald N., "Cytoplasmic Pollen Sterility in Corn," Advances in Genetics, vol. 13, pp. 1-56, 1965.
Bassett, M.J. et al., "Cytoplasmic Male Sterility in Common Bean," J. Amer. Soc. Hort. Sci., vol. 107, No. 5, pp. 791-793, 1982. Barsby, Tina L., "The Transfer of Cytoplasmic Male Sterility to Winter-Type Oilseed Rape (*Brassica napus* L.) by Protoplast Fusion," Plant Science, vol. 53, pp. 243-248, 1987.
Fu, Tingdong et al., "Studies on 'Three Line' Polima Cytoplasmic Male Sterility Developed in *Brassica napus* L.," Plant Breeding, vol. 104, pp. 115-120, 1990.
Prakash, S. et al., "Male sterility caused by cytoplasm of *Brassica oxyrrhina* in *B. campestris* and *B. juncea*," Theoretical and Applied Genetics, vol. 79, pp. 285-287, 1990.
Argumugam, N. et al., "Somatic cell hybridization of 'oxy' CMS *Brassica juncea* (AABB) with *B. oleracea* (CC) for correction of chlorosis and transfer of novel organelle combinations to allotetraploid brassicas," Theoretical Applied Genetics, vol. 100, pp. 1043-1049, 2000.

(Continued)

*Primary Examiner* — David T Fox
(74) *Attorney, Agent, or Firm* — Oliff & Berridge, PLC

(57) ABSTRACT

A cytoplasmic male sterility (CMS) system in different *Brassica* species having a distinct mitochondrial DNA specific RFLP signature. A method for obtaining male sterile lines and restoration of fertility in *B. juncea* for hybrid seed production using the CMS. This CMS in *B. juncea* can be restored by crossing male sterile plants with any *B. juncea* genotype other than the maintainer genotype. The same *B. juncea* genotype acts as maintainer of male sterility after a specified number of backcrosses. The CMS also relates to histological characterization of another and microspore development in *B. juncea*.

6 Claims, 8 Drawing Sheets

OTHER PUBLICATIONS

Figure 1:
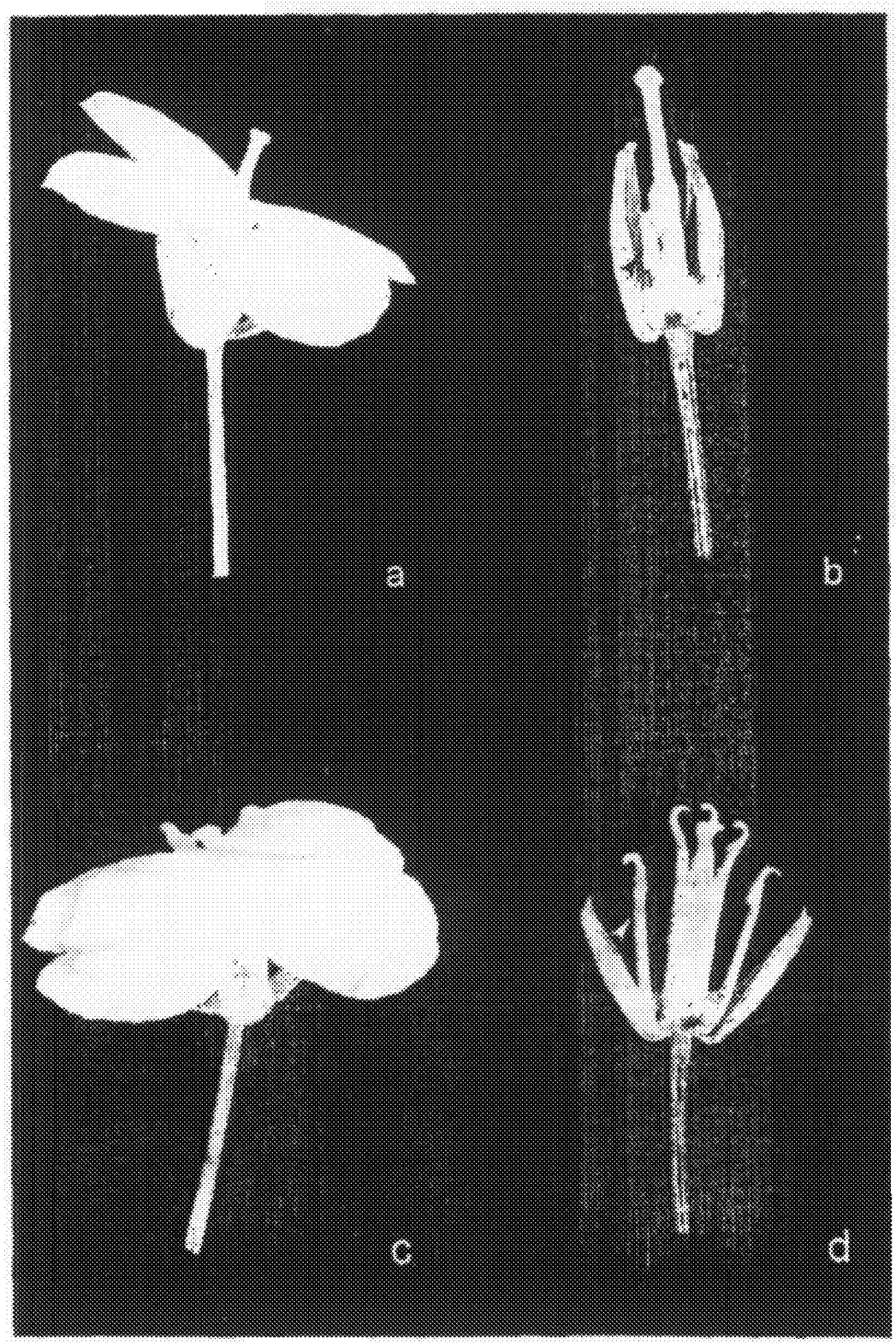

Pradhan, Akshay K. et al., "Identification of the Putative Cytoplasmic Donor of a CMS System in *Brassica juncea*," *Plant Breeding*, vol. 106, pp. 204-208, 1991.

Stiewe, G. et al., "Establishing Cytoplasmic Male Sterility in *Brassica napus* by Mitochondrial Recombination with *B. tournefortii*," *Plant Breeding*, vol. 113, pp. 294-304, 1994.

Arumugam, N. et al., "Synthesis of hexaploid (AABBCC) somatic hybrids: a bridging material for transfer of 'tour' cytoplasmic male sterility to different *Brassica* species," *Theoretical Applied Genetics*, vol. 92, pp. 762-768, 1996.

Rao, G.U. et al., "Development of a New Cytoplasmic Male-Sterility System in *Brassica juncea* through Wide Hybridization," *Plant Breeding*, vol. 112, pp. 171-174, 1994.

Kirti, P.B. et al., "A stable cytoplasmic male-sterile line *Brassica juncea* carrying restructured organelle genomes from the somatic hybrid *Trachystoma ballii + B. juncea*," *Plant Breeding*, vol. 114, pp. 434-438, 1995.

Kirti, P.B. et al., "Transfer of *Ogu* cytoplasmic male sterility to *Brassica juncea* and improvement of the male sterile line through somatic cell fusion," *Theoretical Applied Genetics*, vol. 91, pp. 517-521, 1995.

Pelletier, G. et al., "Intergeneric Cytoplasmic Hybridization in Cruciferae by Protoplast Fusion," *Mol Gen Genet*, vol. 191, pp. 244-250, 1983.

Menczel, Laszlo et al., "Fusion-mediated combination of Ogura-type cytoplasmic male sterility with *Brassica napus* plastids using X-irradiated CMS protoplasts," *Plant Cell Reports*, vol. 6, pp. 98-101, 1987.

Hu, B. et al., "Sterility and variation resulting from the transfer of polima cytoplasmic male sterility from *Brassica napus* into *Brassica chinensis*," *Journal of Agricultural Science*, Cambridge, vol. 128, pp. 299-301, 1997.

Pellan-Delourme et al., "Cytoplasmic male sterility in rapeseed (*Brassica napus* L.): female fertility of restored rapeseed with 'Ogura' and cybrids cytoplasms,"*Genome*, vol. 30, pp. 234-238, 1988.

Delourme, R. et al., "Radish Cytoplasmic Male Sterility in Rapeseed: Breeding Restorer Lines with a Good Female Fertility," *Breeding: Methodology*, P2-019, pp. 1506-1510, 1991.

Kirti, P.B. et al., "Introgression of a gene restoring fertility to CMS(*Trachystoma*) *Brassica juncea* and the genetrics of restoration," *Plant Breeding*, vol. 116, pp. 259-262, 1997.

Prakash, S. et al., "A *Moricandia arvensis*-based cytoplasmic male sterility and fertility restoration system in *Brassica juncea*," *Theoretical Applied Genetics*, vol. 97, pp. 488-492, 1998.

Prakash, S. et al., "Expression of male sterility in alloplasmic *Brassica juncea* with *Erucastrum canariense* cytoplasm and the development of a fertility restoration system," *Plant Breeding*, vol. 120, pp. 479-482, 2001.

Bhat, S.R. et al., "A unique introgression from *Moricandia arvensis* confers male fertility upon two different cytoplasmic male-sterile lines of *Brassica juncea*," *Plant Breeding*, vol. 124, pp. 117-120, 2005.

* cited by examiner

CYTOPLASMIC MALE STERILITY SYSTEM FOR BRASSICA SPECIES AND ITS USE FOR HYBRID SEED PRODUCTION IN INDIAN OILSEED MUSTARD BRASSICA JUNCEA

This application is a 371 of PCT/IN05/00278 filed 22 Aug. 2005.

FIELD OF THE INVENTION

This invention relates to a novel cytoplasmic male sterility (CMS) system in oilseed Brassica species and a method for obtaining male sterile Brassica lines using the said male sterile cytoplasm. The invention also relates, in particular, to a method for using the said male sterility system for the production of hybrid seeds in Brassica juncea.

BACKGROUND OF THE INVENTION

The contribution of hybrids towards enhancing productivity of crop plants through the phenomenon of heterosis or hybrid vigor, in which F1 hybrid plants generated by crosses between two genetically diverse parents exhibit improved yield than either of the parents, is well documented (Banga 1992, In Breeding Oilseed Brassicas Eds. Labana K S, Banga S S and Banga S K, Narosa Publishing House, New Delhi; Pradhan et. al., 1993, Euphytica 69:219-229). Cross pollination is essential for the production of hybrids and hence, it is imperative to render one of the parents male sterile to ensure cross pollination to facilitate the production of hybrid seeds in a commercially viable manner.

One of the ways to induce male sterility is by the use of cytoplasmic male sterility (CMS) systems. Cytoplasmic male sterility (CMS) in plants is a maternally inherited trait, the genetic determinants of which are located in genomes of the cytoplasmic organelle, the mitochondria, and is manifested as a result of incompatibility between the nuclear and mitochondrial genomes. This incompatibility arises mainly due to aberrant recombination events, insertions and deletions in mitochondrial DNA that result in unusual open reading frames (Dewey et. al., 1987, Proc. Natl. Acad. Sci. USA 84:5374-5378; Krishnasamy and Makaroff, 1993, Curr. Genet. 24:156-163). These rearrangements of mitochondrial DNA molecules are widely reported by Bonhomme et. al. (1992, Mol. Gen. Genet. 235:340-348), Janska et. al. (1998, Plant Cell 10:1163-1180) and have also been shown to occur spontaneously in vitro (Vitrat et. al., 1992, Mol. Gen. Genet. 233:193-200; Kanazawa et. al., 1994, Genetics 138:865-870). In most CMS systems, the mitochondrial DNA rearrangements mainly affect the development of male reproductive organs but may also induce some other floral and phenotypic abnormalities. Such plants are severely impaired in their ability to produce functional pollen grains.

CMS provides a useful mechanism for pollination control and commercial hybrid seed production. In crop plants, where seeds are the product of economic value, restoration of fertility in the F1 hybrids is essential. CMS-restorer systems have been used for the production of hybrid seeds in a large number of crops like maize, rice, sorghum, sunflower etc.

CMS may be either alloplasmic or spontaneous in origin. Spontaneous CMS systems arise in breeding lines without intentional intervention. Examples include: the maize T-cytoplasm [Duvick D N: Cytoplasmic pollen sterility in corn. In: Caspari E W, Thoday J M (eds) Advances in Genetics. Vol 13, pp 1-56. Academic Press, New York (1965)]; the pol cytoplasm of B. napus (which arose in cultivar Polima, Fu, 1981, Eucarpia Cruciferae Newsl. 6:6-7) and the male sterile cytoplasm of Phaseolus (first reported by Basset and Shuh, 1982, J. Am. Soc. Hort. Sci. 107:791-793). The 'Pol' CMS has been extensively used to produce CMS lines in oilseed B. napus (Barsby et. al., 1987, Plant Sci. 53:243-248; Fu et. al., 1990, Plant Breeding 104:115-120; Sodhi et. al., 1993, Plant Breeding 110:334-337).

In an alloplasmic CMS system, an alien cytoplasm present in the nuclear background of a cultivated crop variety leads to nuclear—cytoplasmic incompatibility inducing male sterility. Several alloplasmic CMS systems reported in various Brassica species have been generated using wild relatives as the cytoplasmic donors. B. oxyrrhina cytoplasm has been shown to induce male sterility in B. juncea (Prakash and Chopra, 1990, Theor. Appl. Genet. 79: 285-287) and B. napus (Arumugam et. al., 2000, Theor. Appl. Genet. 100:1043-1049). Similarly, B. tournefortii cytoplasm in B. juncea and B. napus (Pradhan et. al., 1991, Plant Breeding 106:204-208; Steiwe and Robellen, 1994, Plant Breeding 113: 294-304; Arumugam et. al., 1996, Theor. Appl. Genet. 92:762-768), Diplotaxis siifolia cytoplasm in B. juncea (Rao et. al., 1994, Plant Breeding 112:171-174), Trachystoma ballii cytoplasm in B. juncea (Kirti et. al., 1995a, Plant Breeding 114:434-438), Raphanus sativus cytoplasm in B. juncea and B. napus (Kirti et. al., 1995b, Theor. Appl. Genet. 91:517-521; Pelletier et. al., 1983, Mol. Gen. Genet. 191: 244-250; Menczel et. al., 1987, Plant Cell Rep. 6:98-101), Moricandia arvensis cytoplasm in B. juncea (Prakash et. al., 1998, Theor. Appl. Genet. 97:488-492) and Erucastrum canariense cytoplasm in B. juncea (Prakash et. al., 2001, Plant Breeding 120:479-482) induces male sterility. A number of alloplasmic CMS systems have also been reported in B. oleracea (Hu et. al., 1997, J. Agric. Sci. 128:299-301, Verma et. al., 2000, Plant Breeding 119:90-92, U.S. Pat. No. 6,046,383, UK Patent No. GB2281568A, WO 96/21010).

However, most of the alloplasmic CMS systems cited above could not be utilized effectively due to lack of corresponding fertility restorer lines that could restore male fertility in the respective F1 hybrids. For such CMS systems, attempts have been made to introgress restorer genes from the respective donors of the cytoplasmic male sterility trait. However, the transfer of restorer genes from wild relatives is often hampered by its linkage to undesirable traits viz. reduced female fertility as observed in 'Ogu' CMS in B. napus (Delourme and Renard, 1988, Genome 30:234-238). This undesirable linkage was subsequently broken in order to develop restorer lines with good female fertility (Delourme et. al., 1991, Proc. 8th Int. Rapeseed Congr. 5:1506-1510, Patent No. CA2273137).

Similar attempts have been made to introduce fertility restorer function from the cytoplasm donor species for various alloplasmic CMS systems available in B. juncea. However, this kind of transfer requires long-winded breeding programs and could falter due to lack of chromosomal exchanges or linkage drag. Kirti et. al. (1997, Plant Breeding 116:259-262) reported the isolation of a restorer plant for Trachystoma ballii CMS with 90% pollen viability. However, the identified restorer plant continued to show leaf serration of T. balli, intermediate flower morphology, contorted pods and yellow cylindrical seeds typical of T. balli, indicating that restoration of Trachystoma ballii CMS is far from being perfect.

Prakash et. al. (1998, Theor. Appl. Genet. 97:488-492) reported isolation of a restorer of another CMS system derived from Moricandia arvensis wherein the restored plant showed 96% pollen viability. However, the restored plants exhibited severe chlorosis similar to CMS plants as well as reduced female fertility. Another alloplasmic CMS system in B. juncea derived from Erucastrum canariense cytoplasm developed by Prakash et. al. (2001, Plant Breeding 120:479-482), also lacked proper restoration. The restored plant showed 90% pollen viability but was also associated with reduced female fertility. Recently Bhat et. al. (2005, Plant Breeding 124:117-120) have shown introgression of restorer from *Moricandia arvensis* into *B. juncea* which restores both *M. arvensis* and *Diplotaxis catholica* cytoplasm.

So far none of the restorer lines isolated for respective alloplasmic CMS systems has shown perfect fertility restoration without any negative effect in terms of morphology, fertility etc. thereby compromising the eventual usage of such lines for the production of hybrid plants and seeds with enhanced yield.

Thus, a need in the art currently exists for developing a cytoplasmic male sterility system along with its restorer for *Brassica* species which is substantially free of phenotypic infirmities and other defects, and can be fully restored and therefore used in producing hybrid seeds in a commercially viable manner. The present invention seeks to fulfill this need.

OBJECTS OF INVENTION

The main object of the invention is to provide a novel cytoplasmic male sterility (CMS) system in oilseed *Brassica*, the said CMS being designated as '126-1 CMS'.

Another object of this invention is to provide methods for developing male sterile *Brassica* lines using the said novel 126-1 male sterile cytoplasm and a method for producing hybrid plants and seeds in *Brassica juncea* using the said CMS system.

DETAILED DESCRIPTION OF THE INVENTION

Accordingly, the invention provides a novel cytoplasmic male sterility (CMS) system, designated as 126-1 CMS. The said system is hereinafter referred to as '126-1 CMS'. The said CMS system was first developed and obtained in a microspore derived doubled haploid population of an Indian *Brassica* variety i.e. *Brassica napus* var ISN 706. The said male sterile plant exhibits normal phenotypic and morphological characteristics as any other plant of genus *Brassica*, species *napus*; except that it does not produce viable pollen grains and is hence, male sterile. Detailed investigation revealed that the origin of the said male-sterility trait may be traced to cytoplasm, as it follows maternal inheritance. This CMS can be transferred to any *B. napus* genotype as well as to *B. juncea* genotype through recurrent back-crossings. The morphological details of the flowers of 126-1 CMS system are shown in FIG. 1 (*a-d*). Henceforth, the term genotype is used to include all the varieties, lines and cultivars of a given or specific *Brassica* species unless otherwise mentioned.

The 126-1 CMS trait is characterized by generation of mitochondrial DNA specific fingerprints in CMS lines of *B. napus* and *B. juncea*. The genetic determinants of cytoplasmic male sterility (CMS) in plants are located in mitochondria. The DNAs of the said 126-1 CMS lines are extracted and restriction enzyme patterns analyzed by RFLP method using certain mitochondrial DNA specific probes. The analysis revealed distinct banding patterns as described below. Similar or identical patterns are observed when the above 126-1 CMS trait is transferred from *B. napus* to *B. juncea* by inter-specific crossing followed by repeated back-crossing to *B. juncea*.

RFLP is a technique wherein the DNA of a plant/organism is digested with a restriction enzyme (i.e. enzymes that cleave DNA molecules at specific nucleotide sequences depending on the enzyme used). The digestion produces DNA fragments of varying lengths which are separated and analyzed by gel electrophoresis. The pattern so generated is unique to the organism/plant and hence, the technique is used to differentiate organisms/plants from each other on this basis.

Accordingly, DNAs of different *B. napus* and *B. juncea* genotypes carrying 126-1 CMS were extracted, subjected to digestion by restriction enzymes and the restriction enzyme patterns were analyzed using mitochondrial specific DNA as probes. The RFLP patterns so generated are depicted in FIGS. 2-7

Figure 2:
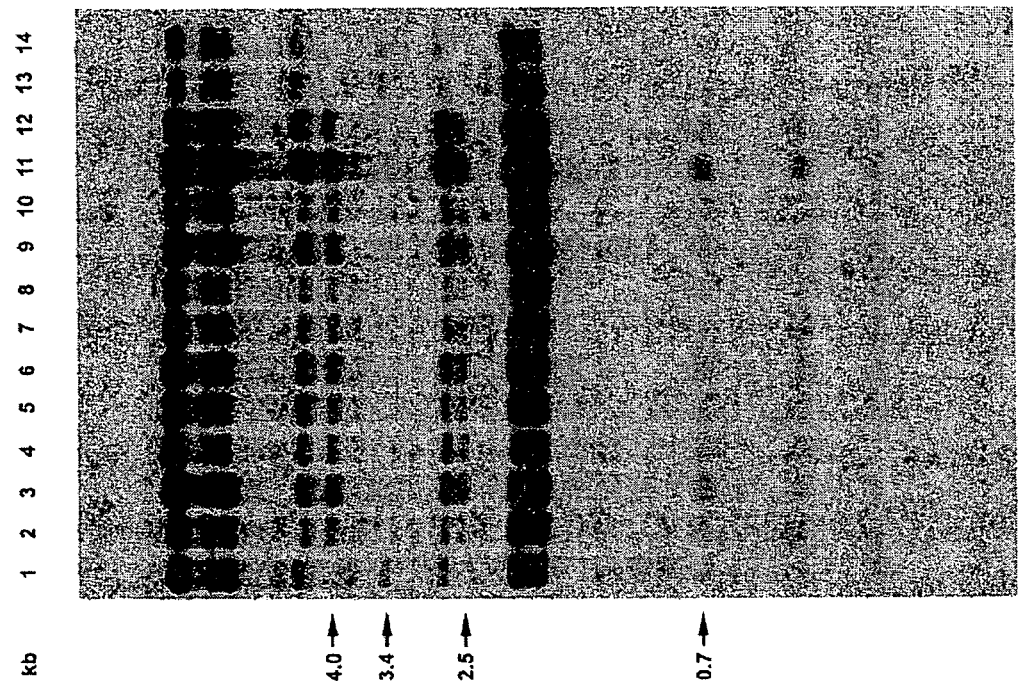
Figure 3:
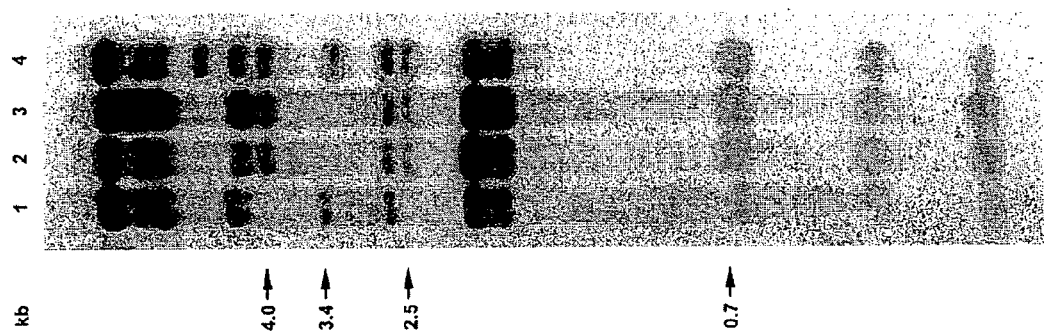

During the said RFLP analysis, the DNAs from the 126-1 CMS genotypes in both *B. napus* and *B. juncea* were digested with EcoRI restriction enzyme and hybridized to cosmid clones, pCos$^{13}$, pCos$^{17}$, and pCos$^{42}$ containing *B. oxyrrhina* mitochondrial DNA as probes. The said three cosmid clones from heterologous system (*B. oxyrrhina*) have been used to cover different regions of the entire mitochondrial DNA genome to reveal any changes in the mitochondrial DNA, which is responsible for male sterility trait and is a determinant of male sterility trait in the present CMS system and the plants to which it is transferred. The said clones have been deposited at the Microbial Type Culture Collection (MTCC), Chandigarh at Accession Nos. 5242 (for pCos$^{13}$), 5243 (for pCos$^{17}$) and 5244 (for pCos$^{42}$). The following RFLP patterns are obtained with these three cosmid clones:

A) A pattern as shown in FIG. 2 (lanes 1 to 14) and FIG. 3 (lanes 1 to 4) when digested with EcoRI as restriction enzyme and hybridized to cosmid clone pCos$^{13}$ containing *B. oxyrrhina* mitochondrial DNA as probe and comprising;
   (i) a first restriction fragment length polymorphism (RFLP) band of about 4.0 kb length which is present in CMS genotypes but absent in parent genotypes;
   (ii) a second restriction fragment length polymorphism (RFLP) band of about 3.4 kb length which is present in parent genotypes but absent from CMS genotypes
   (iii) a third restriction fragment length polymorphism (RFLP) band of about 2.5 kb length which is present in CMS genotypes but absent in parent genotypes; and
   (iii) a fourth restriction fragment length polymorphism (RFLP) band of about 0.7 kb length which is present in CMS genotypes but absent in parent genotypes.

Figure 4:
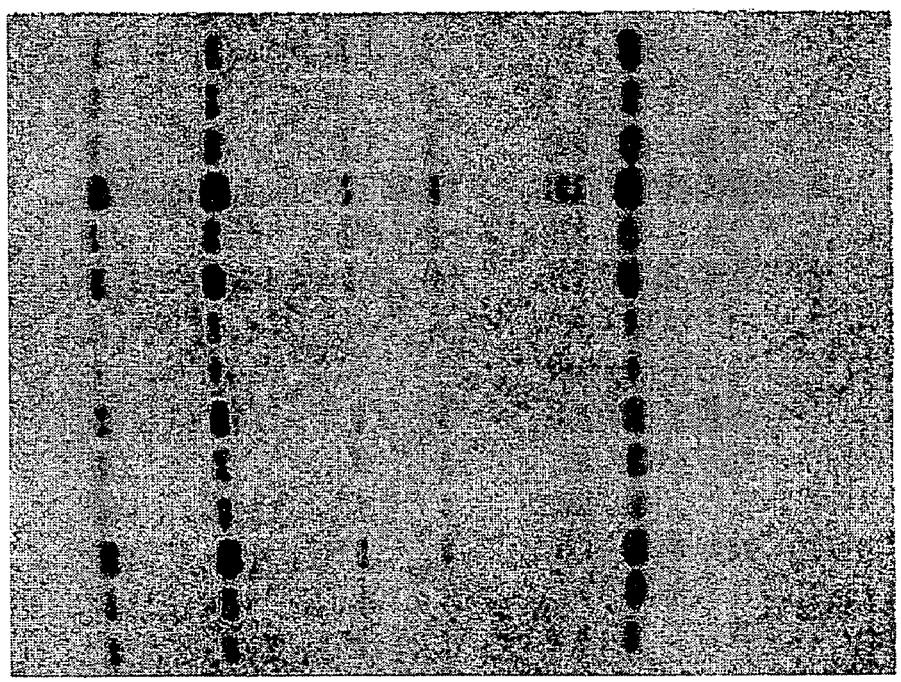
Figure 5:
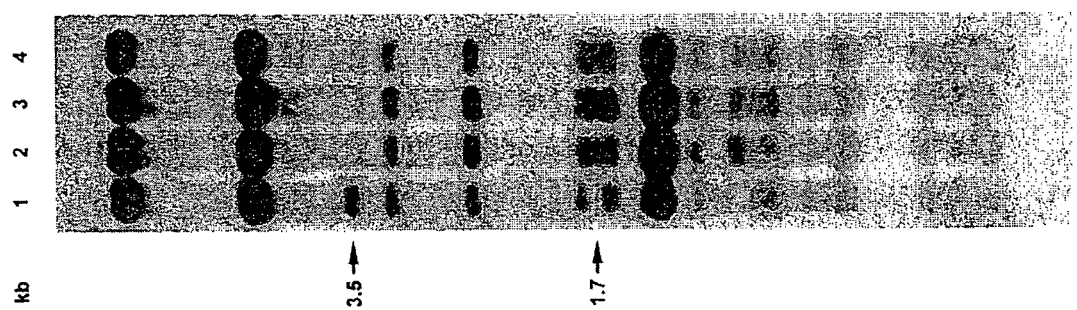

B) An RFLP pattern as shown in FIG. 4 (lanes 1 to 14) and FIG. 5 (lanes 1 to 4) when digested with EcoRI as restriction enzyme and hybridized to cosmid clone pCos$^{17}$ containing *B. oxyrrhina* mitochondrial DNA as probe comprising:
   (i) a parent specific first restriction fragment length polymorphism (RFLP) band of about 3.5 kb length which is present in parent genotypes but absent from CMS genotypes;
   (ii) a second restriction fragment length polymorphism (RFLP) band of about 1.7 kb length which is present in CMS genotypes but absent in parent genotypes.

Figure 6:
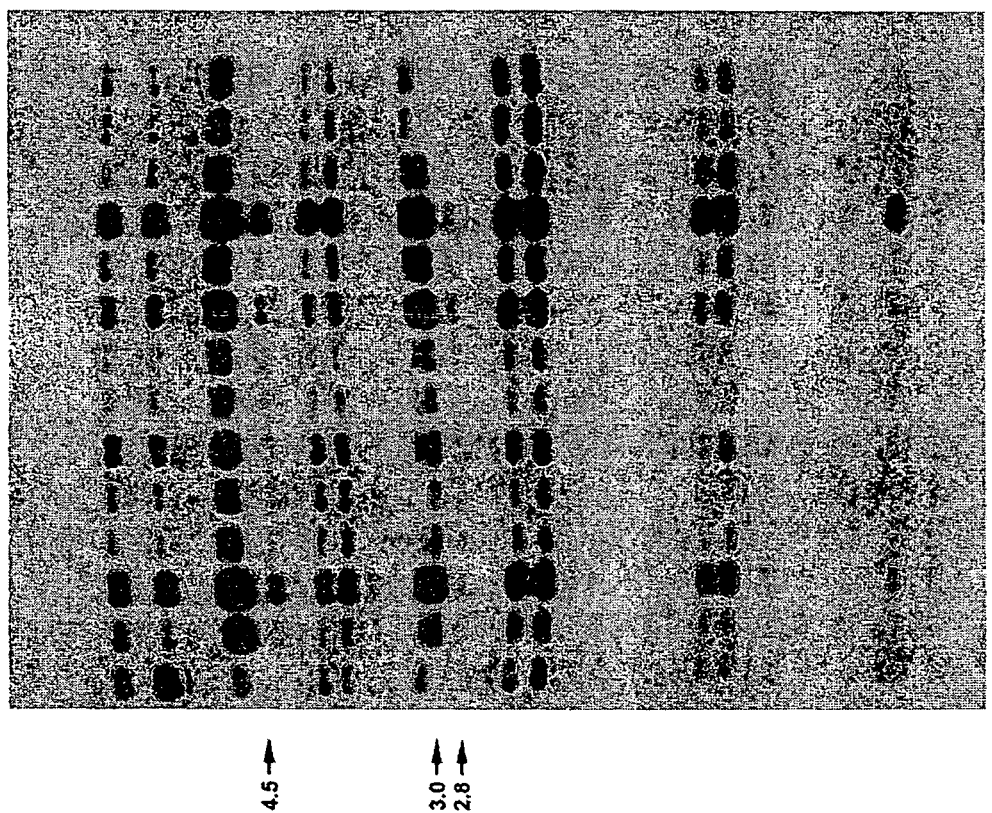
Figure 7:
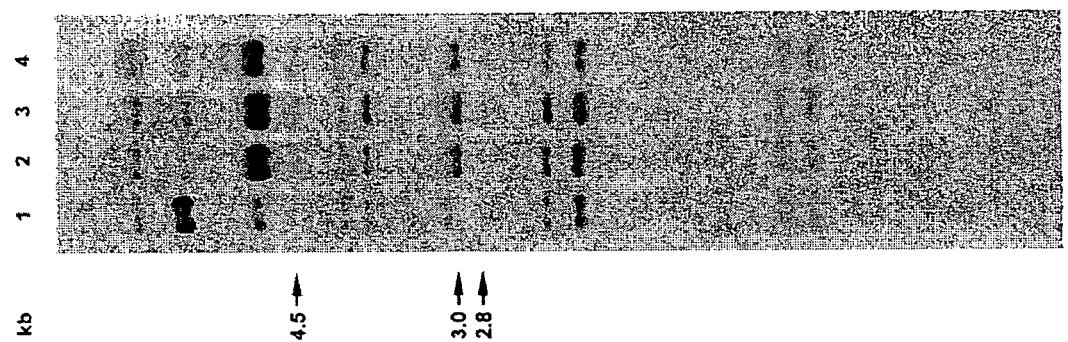

C) An RFLP pattern as shown in FIG. 6 (lanes 1 to 14) and FIG. 7 (lanes 1 to 4) when digested with EcoRI as restriction enzyme and hybridized to cosmid clone pCos$^{42}$ containing *B. oxyrrhina* mitochondrial DNA as probe comprising:
   (i) a first restriction fragment length polymorphism (RFLP) band of about 4.5 kb length which is present in CMS genotypes but absent in parent genotypes;
   (ii) a second restriction fragment length polymorphism (RFLP) band of about 3.0 kb length which is present in CMS genotypes but absent in parent genotypes;
   (iii) a third restriction fragment length polymorphism (RFLP) band of about 2.8 kb length which is present in CMS genotypes but absent in parent genotypes.

Since the banding patterns described above are uniformly observed in the original 126-1 CMS of *B. napus* var. ISN 706 as well as in all the backgrounds to which it is transferred (transferee plants), the said pattern is characteristic of the 126-1 CMS system, and hence is referred to as the '126-1 CMS specific fingerprint' in the description that follows.

The invention also provides a cell of a plant of genus *Brassica* comprising in its cytoplasm the mitochondrial DNA as described above. The plant cell is part of the plant selected from *Brassica juncea, Brassica napus, Brassica carinata, Brassica oleracea, Brassica nigra* and *Brassica campestris*. The male sterile *Brassica juncea* plant, which comprises in its mitochondrial genome a 126-1 CMS specific fingerprint i.e. the RFLP pattern above and shown in any of FIGS. 2, 3, 4, 5, 6, 7.

Thus all the three cosmid clones yield a CMS specific RFLP signature for the identification of 126-1 CMS. The band sizes are calculated on the basis of a standard DNA size markers, based on logarithmic relationship between size of DNA and distance migrated. The marker used in the present study is Lambda DNA digested with restriction enzyme Hind III. Based on the above calculations, the band sizes are usually approximate, hence the band sizes mentioned in the present invention represent an approximate value.

Figure 8:
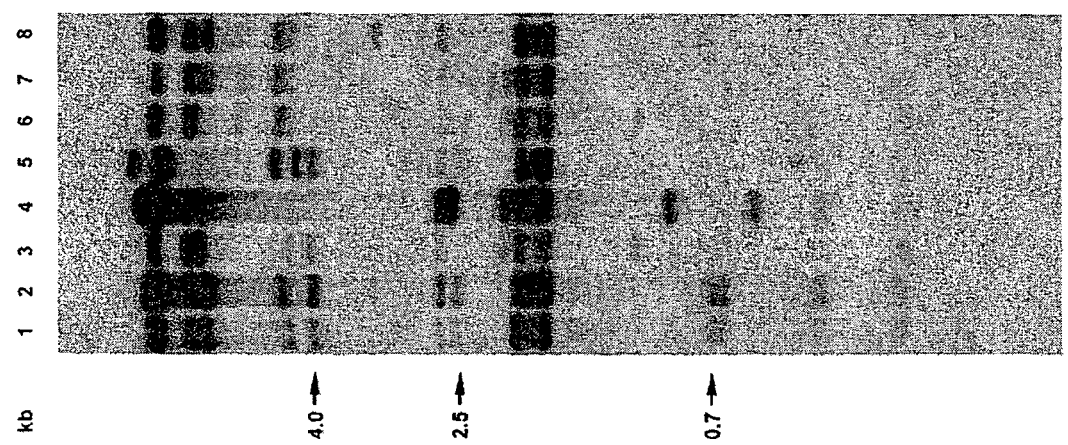

To further differentiate the 126-1 CMS from the other existing CMS systems like Ogura, Tour, Oxy, Moricandia and Diplotaxis, all of these were transferred to *B. juncea* var. Pusa bold background and the DNA of all these was analyzed by RFLP. Hybridization of EcoRI digested DNAs with the cosmid clone pCos[13] show that the banding patterns of all the CMS tested are different from that of the parent and 126-1 CMS Pusa bold. (FIG. 8) indicating the uniqueness of 126-1 CMS. As shown in FIG. 8, the 126-1 CMS exhibits an unique banding pattern (lane 2) as compared to other known CMS systems (lanes 3-8).

Thus, the invention provides a novel CMS system which could be used for the development of hybrid seeds. The seeds of the said novel 126-1 CMS system have been deposited at the International depository at NCIMB on Jun. 29, 2005 at accession no. NCIMB 41331.

The said 126-1 CMS system when crossed with another plant of genus *Brassica* produces male sterile plants. No floral or other phenotypic abnormalities (such as chlorosis) were observed in any of the plants resulting from the cross. In fact, even varying temperature conditions do not have any effect on this male-sterility system. Such progeny plants that receive or inherit the 126-1 CMS cytoplasm together with the 126-1 CMS specific fingerprint are referred to as 126-1 CMS recipient/transferee plants hereafter for sake of convenience.

The said 126-1 CMS exhibits various distinctive characteristics (FIG. 10) which may be discerned at the histological level, some of which are as under:
a) the microspores undergo progressive and rapid degeneration of cell contents after their release from the tetrads;
b) degeneration of microspores precedes the degeneration of tapetal layers surrounding the microspores;
c) leakage of lipid material occurs from the tapetum into the outer periphery of the tapetal layer instead of on the microspores;
d) endothecial layer of the anther comprising flattened cells are marked by the absence of secondary wall thickenings;
e) indehiscent anthers are marked by the absence of stomium and functional endothecial layer;
f) presence of intact interlocular septum.

A skilled person may recognize that there may be minor variations in the histological features amongst genotypes within a species or genus. Hence, at least some of the above features may be present in most of the 126-1 CMS recipient plants with minor variations.

In another aspect, the invention provides a method for developing a male sterile plant comprising the steps of:
a) crossing a *Brassica* plant possessing in its cytoplasm a 126-1 CMS specific fingerprint with a genotype selected from *B. napus* or *B. juncea* lacking the said fingerprint,
b) allowing the plants of step (a) to set seeds, and
c) developing the progeny to a male sterile plant comprising in its cytoplasm the 126-1 CMS specific fingerprint;
d) Optionally, performing repeated backcrosses to the progeny plant of step (c) with the plant of step (a) lacking the 126-1 specific fingerprint.

Following the above method, a number of male sterile plants may be generated by crossing a *Brassica* plant comprising in its cytoplasm mitochondrial DNA with 126-1 CMS specific fingerprint, with a plant of *B. napus* or *B. juncea* lacking the said fingerprint. The plants are allowed to set seed and male sterile progeny is obtained. When this cytoplasmic male sterility is transferred to other *B. napus* varieties through inter-varietal crosses, the F1 generation is completely male sterile and the sterility is stably maintained in subsequent backcrosses. When 126-1 CMS is transferred to *B. juncea* through inter specific crosses, the interspecific F1 plants between *B. napus* carrying 126-1 CMS specific fingerprint and normal *B. juncea* (lacking the specific fingerprint) show partial fertility. When F1 plants are repeatedly back-crossed to the recurrent parent *B. juncea* lacking the 126-1 CMS specific fingerprint, the level of male sterility progressively increases with each back-cross generation. Thus the induction of male sterility is found to be gradual in *B. juncea*, the recipient genotype becoming generally completely male sterile by the BC5 generation or BC6 generation.

By virtue of the methods described above, the male sterility character of the 126-1 CMS may be efficiently transferred from a genotype possessing the 126-1 CMS specific fingerprint to any *Brassica* genotype lacking the said fingerprint. In other words, the 126-1 CMS may be easily transferred to any plant within genus *Brassica* by simply crossing the 126-1 CMS with the desired *Brassica* plant. For example, *Brassica napus* var. 126-1×*Brassica juncea* var. Pusa Bold would result in a male sterile progeny.

Method of Producing Hybrids:

In yet another aspect, the invention provides a method for production of hybrid plants comprising the steps of:
a) crossing a *Brassica juncea* genotype carrying in its cytoplasm the 126-1 CMS specific fingerprint, with another *B. juncea* genotype lacking the said fingerprint,
b) allowing the plants of step (a) to set seeds and harvesting the same,
c) collecting and germinating the seeds to obtain fully fertile hybrid plants.

The above method describes the restoration of male fertility of 126-1 CMS in *B. juncea*. Any *B. juncea* genotype with stable 126-1 CMS when crossed to any other normal male fertile genotype invariably produces fully fertile F1 plants that show normal seed set on selfing indicating that any genotype can be used for obtaining fertile F1 hybrids using 126-1 CMS in *B. juncea* as male sterile line. It has been observed earlier that any genotype can also act as the maintainer of this CMS on repeated backcrossing.

Hence, this method represents an outstanding and unique feature of this 126-1 CMS system in *B. juncea*, wherein the same genotype can be used as the restorer of male fertility in F1 generation for the production of fertile F1 hybrid as well as maintainer of male sterility after a certain number of backcrosses, which is in contrast to all the other CMS-restorer systems reported till date in *B. juncea* or any other *Brassica* species. Thus, contrary to known male sterile systems such as 'Ogura' or 'Polima' or any other similar male sterility system, the genotypes of *Brassica* genus exhibit no phenotypic, morphological or other defects upon receiving the 126-1 CMS specific fingerprint from a donor plant. Further, a special feature of this invention provides the restoration of male fertility in *B. juncea* by crossing any male sterile variety of *B. juncea* with any other normal *B. juncea* variety. On both occasions, i.e. during transfer of 126-1 male sterility character or upon restoration thereof, no morphological or other defects are found in the plant: a feature that makes the 126-1 CMS distinctive.

The above disclosure with reference to the accompanying photographs and examples describes the present invention. A more complete understanding of the invention can be had by reference to the following examples. It is understood that the examples are provided for the purpose of illustrating the invention only, and are not intended to limit the scope of the invention in any way.

BRIEF DESCRIPTION OF THE ACCOMPANYING DRAWINGS

FIG. 1 is a photograph depicting morphological details of male sterile and male fertile flowers; a, male sterile flower of 126-1 CMS in *B. juncea* var. Pusa Bold showing normal flower opening and fully expanded petal formation; b, male sterile flower (petals removed) showing short filaments and shriveled anthers; c, restored male fertile flower showing expanded petal formation and normal flower opening; d, restored male fertile flower (petals removed) showing long filaments and dehiscing anthers.

FIG. 2 is a photograph depicting Southern hybridization pattern of total DNA digested with EcoRI from normal *B. napus* genotype var. ISN 706 (lane 1), 126-1 CMS line of *B. napus* var. ISN 706 (lane 2), 126-1 CMS genotypes of *B. juncea* in the nuclear background of BNF-5 (lane 3), D-205 (lane 4), D-247 (lane 5), DYJ-III (lane 6), Pusa Agrani (lane 7), TM-4 (lane 8), TM-18 (lane 9), Varuna (lane 10), Pusa Bold (lane 11), EH-2 (lane 12), parent *B. juncea* EH-2 (lane 13) and parent Pusa Bold (lane 14) hybridized to cosmid clone pCos$^{13}$ containing *B. oxyrrhina* mitochondrial DNA inserts. Lanes 2 to 12 have mitochondrial DNA specific CMS bands of about 4.0 kb, 2.5 kb and 0.7 kb (RFLP signature bands). The parent specific band of about 3.4 kb present in ISN 706 (lane 1), EH-2 (lane 13) and Pusa bold (lane 14) is missing from 126-1 CMS lines (lanes 2 to 12). The numbers along the left margin of the figure represent a non-linear scale, in kilobase pairs (kb), of DNA fragment sizes.

FIG. 3 is a photograph depicting Southern hybridization pattern of total DNA digested with EcoRI from normal *B. napus* var. ISN 706 (lane 1) and 126-1 CMS lines in the nuclear background of ISN 706 (lane 2), GSL-1 (lane 3) and NU-98 (lane 4) of *B. napus* hybridized to cosmid clone pCos$^{13}$ containing *B. oxyrrhina* mitochondrial DNA inserts. Lanes 2 to 4 have mitochondrial DNA specific CMS bands of about 4.0 kb, 2.5 kb and 0.7 kb (RFLP signature bands). Parent ISN 706 specific band of about 3.4 kb (lane 1) is missing from 126-1 CMS lines (lanes 2 to 4). The numbers along the left margin of the figure represent a non-linear scale, in kilobase pairs (kb), of DNA fragment sizes.

FIG. 4 is a photograph depicting Southern hybridization pattern of total DNA digested with EcoRI from normal *B. napus* var. ISN 706 (lane 1), 126-1 CMS line of *B. napus* var. ISN 706 (lane 2), 126-1 CMS genotypes of *B. juncea* in the nuclear background of BNF-5 (lane 3), D-205 (lane 4), D-247 (lane 5), DYJ-III (lane 6), Pusa Agrani (lane 7), TM-4 (lane 8), TM-18 (lane 9), Varuna (lane 10), Pusa Bold (lane 11), EH-2 (lane 12), parent *B. juncea* EH-2 (lane 13) and parent Pusa Bold (lane 14) hybridized to cosmid clone pCos$^{17}$ containing *B. oxyrrhina* mitochondrial DNA inserts. Parental genotypes ISN 706 (lane 1), EH-2 (lane 13) and Pusa bold (lane 14) were marked by the presence of about 3.5 kb band. 126-1 CMS lines (Lanes 2 to 12) showed the presence of CMS specific band of about 1.7 kb (RFLP signature bands). The numbers along the left margin of the figure represent a non-linear scale, in kilobase pairs (kb), of DNA fragment sizes.

FIG. 5 is a photograph depicting Southern hybridization pattern of total DNA digested with EcoRI from normal *B. napus* var. ISN 706 (lane 1) and 126-1 CMS lines in the nuclear background of ISN 706 (lane 2), GSL-1 (lane 3) and NU-98 (lane 4) of *B. napus* were hybridized to cosmid clone pCos$^{17}$ containing *B. oxyrrhina* mitochondrial DNA inserts. Parental genotype ISN 706 (lane 1) was marked by the presence of about 3.5 kb band. 126-1 CMS lines (Lanes 2 to 4) showed presence of CMS specific band of about 1.7 kb (RFLP signature bands). The numbers along the left margin of the figure represent a non-linear scale, in kilobase pairs (kb), of DNA fragment sizes.

FIG. 6 is a photograph depicting Southern hybridization pattern of total DNA digested with EcoRI from normal *B. napus* var. ISN 706 (lane 1), 126-1 CMS line of *B. napus* var. ISN 706 (lane 2), 126-1 CMS genotypes of *B. juncea* in the nuclear background of BNF-5 (lane 3), D-205 (lane 4), D-247 (lane 5), DYJ-III (lane 6), Pusa Agrani (lane 7), TM-4 (lane 8), TM-18 (lane 9), Varuna (lane 10), Pusa Bold (lane 11), EH-2 (lane 12), parent *B. juncea* EH-2 (lane 13) and parent Pusa Bold (lane 14) hybridized to cosmid clone pCos$^{42}$ containing *B. oxyrrhina* mitochondrial DNA inserts. Lanes 2 to 12 have mitochondrial DNA specific CMS bands about of 4.5 kb, 3.0 kb, and 2.8 kb (RFLP signature bands). CMS specific bands are missing from lanes 1, 13 and 14 representing parental genotypes ISN 706 (lane 1), EH-2 (lane 13) and Pusa bold (lane 14), respectively. The numbers along the left margin of the figure represent a non-linear scale, in kilobase pairs (kb), of DNA fragment sizes.

FIG. 7 is a photograph depicting Southern hybridization pattern of total DNA digested with EcoRI from normal *B. napus* var. ISN 706 (lane 1) and 126-1 CMS lines in the nuclear background of ISN 706 (lane 2), GSL-1 (lane 3) and NU-98 (lane 4) of *B. napus* hybridized to cosmid clone pCos$^{42}$ containing *B. oxyrrhina* mitochondrial DNA inserts. Lanes 2 to 4 have mitochondrial DNA specific CMS bands of about 4.5 kb, 3.0 kb, and 2.8 kb (RFLP signature bands). CMS specific bands are missing from parental line ISN 706 (lane 1). The numbers along the left margin of the figure represent a non-linear scale, in kilobase pairs (kb), of DNA fragment sizes.

FIG. 8 is a photograph depicting Southern hybridization pattern of total DNA digested with EcoRI from various CMS lines available in *B. juncea* background. 126-1 CMS line of *B. napus* genotype ISN 706 (lane 1), 126-1 CMS line of *B. juncea* in the nuclear background of Pusa Bold (lane 2), 'Ogura' CMS in the nuclear background of Pusa Bold (lane 3), 'oxy' CMS in Pusa Bold background (lane 4), 'Diplotaxis' CMS in Pusa Bold background (lane 5), 'Tour' CMS in the nuclear background of Pusa Bold (lane 6), 'Moricandia' CMS in the Pusa Bold background (lane 7), normal Pusa Bold parent (lane 8) hybridized to cosmid clone pCos$^{13}$ containing *B. oxyrrhina* mitochondrial DNA insert. Lanes 3 to 7 have mitochondrial DNA specific banding pattern with pCos$^{13}$ different from the lanes 1 & 2. The numbers along the left margin of the figure represent a non-linear scale, in kilobase pairs (kb), of DNA fragment sizes.

FIG. 9 is a photograph depicting light micrographs of microspores stained with Alexander's stain. a, c microspores from male fertile flowers. b, d microspores from male sterile flowers. a: microspore from male fertile flowers after release from tetrad stains intense red (×40), b: microspores released from male sterile flower have plasmolysed cytoplasm staining red and outer exine staining green (×40), c: microspore from male fertile flower at anthesis showing a thin exine enclosing a deep red cytoplasm (×40), d: microspores from male sterile flower appeared as empty sporoderms (×40).

FIG. 10 is a photograph depicting light micrographs of thin sections of anthers from male fertile (a, c, e) and male sterile buds (b, d, f). a: toluidine stained anther locule of male fertile flower containing well developed microspores (arrow head) surrounded by well differentiated tapetum and outer wall layers (×20), b: toluidine stained anther locule of male sterile flower showing degenerated microspores comprising plasmolyzed cytoplasm and irregular exines. Tapetal cells are vacuolated (×20), c: section showing autofluorescence of lipids in normal male fertile flowers. Microspores appear bright yellow. Endothecial layer is well differentiated showing secondary wall thickenings (arrow head) (×20), d: section of male sterile anther showing sporopollenin (L) leaking from the tapetal cells (T) into the outer periphery. Anther locule is filled with degenerated microspores (×20), e: section showing dehisced anther in normal male fertile flowers with prominent stomium (*) and anther locule filled with well developed microspores (×20), f: section of mature male sterile flower showing indehiscent anther with collapsed locule containing empty sporoderms. Stomium is absent and interlocular septum (>) is intact (×10).

EXAMPLES

Plant Materials

Some of the genotypes used in the present invention along with their characteristics and utility are summarized in Table 1. All the genotypes used are obtained from various repositories open and accessible to the public such as National Bureau of Plant Genetic Resources, Delhi, India. Even otherwise, the germplasm used in the present invention may be easily obtained from other public source depositories. All the germplasm used was either grown under short-day (duration of photoperiod is of 10 hrs) conditions during the normal mustard growing season (October-March) in village Jaunti, Delhi, India or under long-day (duration of photoperiod is of 14 hrs) conditions at Leh, Jammu & Kashmir, India during summer (May-September).

TABLE 1

Varieties and genotypes used in the present invention.

| Species | Line | Characteristic |
|---|---|---|
| B. juncea | BNF-5 | Breeding line |
| | D-205 | Breeding line |
| | D-247 | Breeding line |
| | DYJ-III | Breeding line |
| | EH-2 | Breeding line |
| | Pusa Bold | Released variety |
| | Pusa Agrani | Released variety |
| | TM-4 | Released variety |
| | TM-18 | Released variety |
| | Varuna | National check variety |

TABLE 1-continued

Varieties and genotypes used in the present invention.

| Species | Line | Characteristic |
|---|---|---|
| B. napus | ISN-706 | Indian synthetic napus |
| | GSL-1 | Released variety |
| | NU-98 | Mutant of cv. Westar |

Example 1

Development of 126-1 CMS

Production of doubled haploid plants in B. napus var. ISN 706 was done by essentially following the protocol described by Moellers et. al. (1994, Euphytica 75:95-104).

a) In Vivo Growth Conditions:

The seeds of B. napus var. ISN 706 were sown and plants were established in a plant growth chamber at a day/night temperature of 20° C./15° C. under a 10 h photoperiod for about 40 days till the emergence of inflorescence axis. Thereafter the plants were shifted to a day/night temperature of 10° C. to 5° C. under a 14 h photoperiod for at least 15 days before harvesting buds for microspore isolation.

b) Microspore Isolation:

40 to 60 flower buds, each of 3-4 mm length were harvested. The buds were washed in mild detergent solution followed by washing in running water for 15 minutes. Then the buds were treated with 70% ethanol for 5 minutes and washed once with sterile distilled water. Subsequently, the buds were sterilized with sodium hypochlorite solution containing 4% free chlorine for 10 min and the sterilizing solution was removed by washing the buds thoroughly three times with sterile distilled water. The buds were then transferred to a sieve fitted with double layer of stainless steel mesh (40 μm mesh below and 150 μm mesh above) and gently crushed using a ground glass in a suitable volume (10 ml) of wash medium (WM, modified from Lichter, 1982, Z. Pflazenphysiol 105:427-434). The microspore suspension was transferred to sterile screw capped tubes and spun at 1000 rpm for 5 minutes. Then the microspores were washed once in fresh WM. The microspores were resuspended in 2-10 ml NLN (Lichter, 1982, Z. Pflazenphysiol 105:427-434) with 13% sucrose (13NLN) and the yield was estimated using a haemocytometer.

The Lichter medium comprises the following salts:

| | Concentration (mg/l) |
|---|---|
| Major salts*$^{WM}$ | |
| Ca(NO$_3$)$_2$•4 H$_2$O | 500 mg |
| MgS0$_4$•7 H$_2$O | 125 mg |
| KH$_2$PO$_4$ | 125 mg |
| KNO$_3$ | 125 mg |
| Iron salts | |
| Fe-EDTA(Ferric monosodium EDTA) | 40 mg |
| Amino acid/derivatives*$^{WM}$ | |
| L-Glutamine | 800 mg |
| Serine | 100 mg |
| Glutathione | 30 mg |
| Vitamins | |
| Glycine | 2.0 |
| Nicotinic acid | 5.0 |

-continued

| | Concentration (mg/l) |
|---|---|
| Pyridoxine | 0.5 |
| Thiamine | 0.5 |
| Folic Acid (dissolve in KOH) | 0.5 |
| Biotin | 0.5 |
| Minor elements (as in MS )*$^{WM}$ | 2 ml |
| Sucrose*$^{WM}$ | 130 g |

*$^{WM}$Wash medium constituents (pH 5.8-6.0)

The suspension volume was adjusted to 4 ml with a microspore density of $8\times10^4$/ml and 1 ml of 25 mg/50 ml colchicine in 13NLN (final colchicine concentration is 0.01%) was added.

c) Microspore Culture:

The microspore suspension was incubated in 5 ml 13NLN with colchicine at 28.0° C. for 24 h in dark. Colchicine was washed off with 13NLN. Microspores were plated at a density of $4\times10^4$ microspores/ml in petridishes containing 1% activated charcoal prepared in 13NLN and incubated at 28.0° C. for 7-10 days. The plates with floating embryos were shifted on to a shaker at 80 rpm, 16 h light and 22° C. for 21 days. The 21-days old embryos were transferred to 13NLN containing 0.015 mM (3.96 mg/l) ABA and incubated in an environmental shaker at 80 rpm, 15° C. and 10 h photoperiod for 14 days.

d) Regeneration of the Microspore Derived Embryos:

Embryos were transferred to semisolid Schenk medium (Schenk and Robbelen, 1982, Z. Pflanzenzuchtg 89:278-288) with 1 mg/l $GA_3$ for germination. The shoot tips from the seedlings were subcultured (after 1-2 weeks) on MS medium with 2 mg/l IBA for multiplication. The shoots rooted on this medium within 7-10 days and were maintained on the same medium till transfer to the field.

e) Ploidy Analysis:

The regenerated plants were analysed for ploidy level using flow cytometer (Facscan) following Arumuganathan and Earle (1991, Plant Mol. Bio. Rep. 9:229-241). Nuclei from young ($3^{rd}$ or $4^{th}$ leaves from the apex) leaves were isolated and stained with propidium iodide prior to analyzing these in the facscan machine.

f) Identification of the 126-1 CMS Plant:

Out of a population of about 5000 doubled haploid plants transferred to the field one plant was found to be male sterile in which seed set was normal. This plant was crossed with the pollen from male fertile plant of *B. napus* var. ISN 706. The seeds were harvested and sown in the next growing season. All the plants were found to be male sterile. This process was repeated for two more generations and the male sterility was stably inherited indicating the inheritance of the male sterility character to be of maternal origin. The seeds of 126-1 CMS are deposited at NCIMB on Jun. 29, 2005.

Example 2

Analysis of the Male Sterility Status of 126-1 CMS

Plants obtained in example 1 were monitored for male sterility by bagging each plant with a pollination bag to study the seed set on self pollination. Two to three inflorescences bearing 10-15 unopened buds were selfed in each plant. Absence of seed set was taken as a confirmation of male sterility.

Example 3

Estimation of Pollen Viability of 126-1 CMS

Pollen viability was estimated by taking anthers from five randomly chosen flowers and staining the microspores with flourescein diacetate (FDA) as discussed by Heslop-Harrison et. al. (1984, Theor. Appl. Genet. 67:367-375). FDA solution was prepared by dissolving 10 mg of FDA in 20 ml of acetone solvent. Two or three drops of FDA solution were added to 2 ml of 18% sucrose solution to prepare the stock solution. All the 6 anthers of a flower were squeezed in a drop of FDA solution on a glass slide to release the pollen grains. The pollen grains were observed under fluorescent light. Viable pollens fluoresce green and the viability was scored by counting the number of fluorescing pollen grains as against the total number of microspores in a microscopic field.

Example 4

Transfer of 126-1 CMS to Various *Brassica* Genotypes

This cytoplasmic male sterility was transferred through inter-varietal crosses to other genotypes of *B. napus* e.g. GSL-1 and NU 98 which were found to be completely sterile in F1 generation and the sterility was stably maintained in subsequent backcrosses. The 126-1 CMS was also transferred to other *Brassica* species through inter specific crosses followed by recurrent back-crossings. In *B. campestris*, this CMS was transferred to both brown seeded and yellow seeded genotypes of Indian and exotic origin. The F1 progeny resulting from cross between *B. napus* carrying the 126-1 CMS and *B. campestris* was found to be completely male sterile. No other floral or phenotypic abnormalities were observed in any of these crosses. The sterility was found to be stably inherited in successive back-cross generations. In *B. oleracea*, the 126-1 CMS was transferred to both early and late flowering genotypes. The F1 plants turned out to be completely male sterile. However, the F1 plants showed intermediate phenotype and typical curd formation was not observed. The male sterility was stably inherited in successive back-crosses. The curd formation showed improvement with progressive back-crossings.

On transfer of this 126-1 CMS from *B. napus* to different *B. juncea* genotypes, it was observed that the F1 plants are invariably fully fertile and set seeds on selfing unlike the 126-1 CMS recipients in *B. napus* or any other Brassica species with alloplasmic CMS where the F1 plants are always sterile. The induction of male sterility was found to be gradual in *B. juncea*, i.e. the percentage of sterile pollen grains increased with progressive back-crossing, the recipient variety becoming completely male sterile generally by the BC5/BC6 generation. Sterility once achieved is observed to be stable over generations and hence the genotype can be said to act as the maintainer of this CMS. As an example, *B. juncea* genotypes BNF-5, D-205, D-247, TM-4, TM-18 were completely male sterile after BC4 generation. Genotype EH-2 was completely male sterile by BC6 whereas Pusa Bold and Varuna were completely male sterile by BC5 and BC7 generation, respectively. Pollen viability status of different *B. juncea* genotypes has been summarized in Table 2 below:

TABLE 2

Status of pollen viability of various *B. juncea*
varieties and genotypes with 126-1 CMS.

| Genotype | Backcross generation | % pollen viability |
|---|---|---|
| BNF-5 | BC4 | 0.00 |
| D-205 | BC4 | 0.00 |
| D-247 | BC4 | 0.00 |
| DYJ-III | BC2 | 0.00 |
| EH-2 | BC6 | 0.00 |
| Pusa Agrani | BC4 | 1.08 |
| TM-4 | BC4 | 0.00 |
| TM-18 | BC4 | 0.00 |
| Varuna | BC7 | 0.00 |
| Pusa Bold | BC5 | 0.00 |

Example 5

Molecular Fingerprinting of 126-1 CMS a) Isolation of Total DNA:

Total DNA was isolated from fully expanded leaves of *B. napus* var. ISN 706, *B. napus* var. ISN 706 (126-1 CMS), GSL-1, NU-98, *B. juncea* var. Pusa Bold, *B. juncea* var. EH-2, 126-1 CMS *B. juncea* recipient genotypes BNF-5, D-205, D-247, DYJ-III, Pusa Agrani, TM-4, TM-18 and Varuna following the protocol of Rogers and Bendich, (1994, In Plant Mol. Biol. Manual, Gelvin and Schilperoot, Eds. Kluwer academic Publishers). DNA was also extracted from the leaves of various other CMS systems like 'Ogura', 'oxy', 'Diplotaxis', 'Tour' and 'Moricandia in the background of *B. juncea* var. Pusa bold. One gram of leaf tissue was finely powdered in liquid nitrogen and homogenized in 5 ml extraction buffer containing 100 mM Tris-HCl, pH 8; 20 mM EDTA, pH 8; 1.4 M NaCl, 1% PVP40 and 2% CTAB. The above material was incubated at 65° C. for 10 min with occasional shaking followed by extraction with an equal volume of chloroform:isoamylalcohol (24:1). To the supernatant obtained above, 1.25 ml of 10% CTAB solution was added followed by extraction with an equal volume of chloroform: isoamylalcohol. Genomic DNA was precipitated from the above supernatant by addition of 3 volumes of precipitation buffer (50 mM Tris-HCl pH 8.0, 10 mM Sodium EDTA and 1% CTAB) followed by incubation at room temperature for 30 minutes. The pellet obtained was dissolved in 500 µl of buffer containing 10 mM Tris-HCl pH 8.0, 1 mM Sodium EDTA and 1 M Sodium Chloride. Undissolved impurities were removed from above samples by centrifugation followed by precipitation of dissolved DNA using 100% ethanol. The DNA pellet was washed with 70% ethanol and finally dissolved in an appropriate amount of sterile distilled water.

b) Protocols for Restriction Digestion and Southern Hybridization:

Five µg of total DNA was digested overnight at 37° C. with EcoRI restriction endonucleases in a 40 µl reaction volume containing 30u of restriction enzyme in 1× reaction buffer as supplied by the supplier. The digested DNA was electrophoresed on a 0.8% agarose gel and transferred to nylon membranes after treating the gel with denaturation (0.2M NaOH, 6M NaCl) and neutralization (0.5M Tris-HCl, pH 7.5, 1.5M NaCl) solutions.

Southern hybridization was done by treating the membrane for 6 h at 42° C. in prehybridization buffer containing 50% formamide, 0.1% Denhardt's solution, 5×SSC, 5% Dextran sulphate, 1% SDS and 200 ng of Salmon sperm DNA. Labelled probes were prepared using Amersham multiprime labelling kit following manufacturer's instructions. Following prehybridization, the labelled probe was denatured and added to the membrane. The membrane was then hybridized for 16 h at 42° C. After hybridization, the membranes were washed twice in 2×SSC for 15 min. at room temperature and once at 30° C. in 0.2×SSC, 0.1% SDS at 65° C. Subsequently the membranes were exposed overnight to X-ray film (Kodak, X-Omat). The banding patterns were resolved by developing these X-ray films.

c) Analysis of Mitochondrial DNA Composition:

For analyzing mitochondrial DNA, total DNA was digested with EcoRI and hybridized to overlapping cosmid clones (pCos[13], pCos[17] and pCos[42]) containing *B. oxyrrhina* mitochondrial DNA as inserts (Arumugam et. al., 1996, Theor. Appl. Genet. 92:762-768). The results of the analysis are shown in FIGS. 2-7.

d) Results of Analysis:

With clone pCos[13], 126-1 CMS recipient lines of both *B. juncea* and *B. napus* show the presence of CMS specific bands of about 4.0 kb, 2.5 kb and 0.7 kb (FIG. 2 lanes 2 to 12, FIG. 3 lanes 2 to 4) whereas these bands are completely missing from the parental lines of *B. napus* and *B. juncea* (lanes 1, 13 & 14 of FIG. 2 and lane 1 of FIG. 3) indicating that these bands are specific to 126-1 CMS and serve as RFLP signature for identification of 126-1 CMS. A parent specific band of about 3.4 kb (lanes 1, 13 and 14 of FIG. 2 and lane 1 of FIG. 3) is absent from the 126-1 CMS lines of *B. juncea* and *B napus* (FIG. 2 lanes 2 to 12 and FIG. 3 lanes 2&3). However, 126-1 CMS line of NU-98 (FIG. 3 lane 4) showed the presence of about 3.4 kb band as well as an additional band of about 4.6 kb indicating that mitochondrial rearrangements or stoichiometric changes in mitochondrial DNA might have taken place during the transfer of 126-1 CMS recipient from *B. napus* ISN706 to *B. napus* NU98.

Cosmid clone pCos[17] on hybridization with EcoRI digested DNAs of *B. juncea* and *B. napus*, showed the presence of a parent specific band of about 3.5 kb, which is absent from the 126-1 CMS lines (lanes 2 to 12 of FIG. 4 and lanes 2 to 4 of FIG. 5) and a CMS specific band of about 1.7 kb which is absent from the parental lines of *B. juncea* and *B. napus* (FIG. 4 lanes 1, 13 & 14 and FIG. 5 lane 1).

Hybridization of EcoRI digested DNAs of *B. juncea* and *B. napus* lines with the cosmid clone pCos[42] showed the presence of CMS specific bands of about 4.5 kb, 3.0 kb and 2.8 kb (FIG. 6 lanes 2 to 12 and FIG. 7 lanes 2 to 4) which are absent from the parental lines ISN 706, Pusa Bold and EH-2 (FIG. 6 lanes 1, 13 & 14 and FIG. 7 lane 1). Thus all the three cosmid clones give CMS specific RFLP fingerprint for the identification of 126-1 CMS.

Example 6

Histology of Anther and Microspore Development in 126-1 CMS *B. juncea*

Microspore development was studied by Alexander's stain (Alexander, 1969, Stain Technol. 44:117-122). Using this procedure visual distinction can be made between the viable and aborted microspores. Alexander's stain was prepared by mixing 2 ml of glacial acetic acid, 25 ml of glycerol and 50 ml of distilled water. To the above solution, 5 g crystals of Phenol and Chloral hydrate were added. Further, 1 ml of Malachite green (1% in 95% ethanol), 5 ml of acid Fuschin (1% in water) and 0.5 ml of Orange G (1% in water) were added to the above solution. For studying the histology of the developing anthers, buds at different stages of development were fixed in Karnovsky's fixative (Karnovsky, 1965, J. Cell Biol. 27: 137a) overnight at 4° C. Subsequently, samples were dehydrated through ethanol series and embedded in glycol methacrylate resin. Karnovsky's fixative was prepared by dissolving 2 g of paraformaldehyde in 25 ml of distilled water at 60-70° C. One to two drops of 1N NaOH were added to clear the solution. To this solution 5 ml of glutaraldehyde was added and volume was made up to 50 ml with 0.1 M Cacodylate buffer. To 50 ml of this solution, 125 mg of $CaCl_2$ was added. pH of the Karnovsky's fixative stock solution was set at 7-7.2 by using 1N NaOH. Semi-thin sections (3-4 μm) were cut on a rotary microtome. Slides were stained in Toluidine blue O (O'Brien & McCully 1981 Termarcarphi Pty. Ltd. Melbourne Australia). Autofluorescence of sporopollenin and lignified tissue was visualized under UV light microscope (Olympus).

Histological studies on anthers of 126-1 CMS *B. juncea* (var. Pusa bold) along with *B. juncea* (var. Pusa bold) control plants was carried out. Squash preparations of anthers from control and CMS flowers at early stages of development, stained with acetocarmine, observed under light microscope, revealed normal meiotic divisions and development of the microspores till the tetrad stage (figures not shown). Further studies on microspore development were done using Alexander's stain which was prepared as described above.

Squash preparations of anthers from control and CMS flowers at different stages of development were stained with Alexander's stain and observed under light microscope. Microspores in male-fertile flowers exhibited densely stained deep red (Fuschia) cytoplasm (FIG. 9a). As development proceeds, the exine (outer layer) becomes prominent/distinct and stains green (Malachite green) in contrast to the inner cytoplasm which stains red (FIG. 9c). However, in male sterile flowers, the microspores after their release from the tetrads, undergo progressive degeneration of cell contents, exhibiting a crumpled mass with red stain only in the centre of the microspore enclosed by the green exine (FIG. 9b). In mature male sterile flowers, the degenerated microspores appeared as empty sporoderms with irregularly shaped green exines (FIG. 9d).

Anatomical studies were done to follow the development of the anther vis-à-vis microspore development. Buds at different stages of development were fixed in appropriate reagents, processed, sectioned at 3-4μ thickness and stained with Toluidine Blue O following O'Brien & McCully (1981, Termarcarphi Pty. Ltd. Melbourne Australia). Semi-thin sections of anthers were visualized under light microscope. Cross-section of anthers from control male fertile buds (measuring 4-5 mm, stage at which microspores have been released from the tetrads) showed a well developed tapetum layer surrounding uninucleate microspores. Tapetum at 4-5 mm bud stage was intact and stained uniformly (FIG. 10a). In comparison, anthers from the CMS flower buds of 4-5 mm size showed plasmolysed microspores with irregular exines. Tapetal cells stained denser, showed vacuolation and developed intercellular spaces (FIG. 10b). Thus the degeneration of microspores seems to precede the degeneration of the tapetal layer.

Senescing tapetum in *Brassicaceae* is characterized by high lipid content which can be visualized by its autofluorescence under UV light. Cross section of male fertile anthers (6-7 mm in size) revealed that the lipid material from the degenerating tapetum was deposited around the microspores which fluoresce very brightly (FIG. 10c). In the male sterile anthers, the lipid material leaked into the outer periphery of the tapetal layer (FIG. 10d) and the anther locule was filled with empty exines. The endothecial layer was observed to be well developed with secondary wall thickenings in the normal male fertile anthers (FIG. 10c) and at maturity, the dehisced anther was characterized by the presence of stomium and the absence of interlocular septum (FIG. 10e). In the male sterile anthers the endothecial layer was made up of only flattened cells and lacked secondary wall thickenings (FIG. 10d). The indehiscent anthers were also characterized by the absence of stomium and functional endothecial layer and the interlocular septum did not rupture (FIG. 10f).

Anther development in 126-1 CMS differs significantly from another well described alloplasmic CMS system 'Ogu', in *B. napus* (Gourret et. al., 1992, Theor. Appl. Genet. 83:549-556). In 126-1 CMS, normal development of the microspores continues till the tetrad stage. Secondly, degeneration of microspores is independent of tapetal degeneration. The tapetal cells remain intact in 126-1 CMS till the tetrad stage. In the 'Ogu' cytoplasm the tapetum consists of abnormally light vacuolated cells, a sign of degenerating tapetum. The leakage of lipid materials into the outer periphery of tapetal layer is also a characteristic feature of 126-1 CMS. So far no reports are available on anther development and anatomical details in other alloplasmic CMS systems developed in *B. juncea*.

Advantages

1) The present invention provides a novel cytoplasmic male sterility (126-1 CMS) system in *B. napus* and *B. juncea* with a mitochondrial DNA specific RFLP signature.

2) 126-1 CMS is a unique cytoplasmic male sterile system in *B. juncea* wherein any *B. juncea* genotype can be used as a restorer for obtaining fertile F1 hybrid and also as a maintainer of male sterility after a specified number of backcrosses. This 126-1 CMS is free from any other phenotypic or floral abnormalities. Restoration of fertility is complete and does not suffer from any abnormalities usually associated with restorers derived from alloplasmic CMS systems.

We claim:

1. A cell of a plant of genus *Brassica* comprising, in its cytoplasm, a mitochondrial DNA exhibiting the following restriction fragment length polymorphism (RFLP) patterns under hybridization conditions:

A) a first RFLP pattern, such that when the mitochondrial DNA is digested with EcoRI as restriction enzyme and hybridized to cosmid clone pCos[13] (MTCC 5242) containing *B. oxyrrhina* mitochondrial DNA as probe, the pattern comprises:
  (i) a first restriction fragment length polymorphism band of about 4.0 kb length which is present in CMS genotypes but absent in parent genotypes,
  (ii) a second restriction fragment length polymorphism band of about 3.4 kb length which is present in parent genotypes but absent from CMS genotypes,
  (iii) a third restriction fragment length polymorphism band of about 2.5 kb length which is present in CMS genotypes but absent in parent genotypes, and
  (iv) a fourth restriction fragment length polymorphism band of about 0.7 kb length which is present in CMS genotypes but absent in parent genotypes;

B) a second RFLP pattern, such that when the mitochondrial DNA is digested with EcoRI as restriction enzyme and hybridized to cosmid clone pCos[17] (MTCC 5243) containing *B. oxyrrhina* mitochondrial DNA as probe, the pattern comprises:
  (i) a first restriction fragment length polymorphism band of about 3.5 kb length which is present in parent genotypes but absent from CMS genotypes, and (ii) a second restriction fragment length polymorphism band of about 1.7 kb length which is present in CMS genotypes but absent in parent genotypes; and C) a third RFLP pattern, such that when the mitochondrial DNA is digested with EcoRI as restriction enzyme and hybridized to cosmid clone pCos$^{42}$ (MTCC 5244) containing *B. oxyrrhina* mitochondrial DNA as probe, the pattern comprises:
(i) a first restriction fragment length polymorphism band of about 4.5 kb length which is present in CMS genotypes but absent in parent genotypes,
(ii) a second restriction fragment length polymorphism band of about 3.0 kb length which is present in CMS genotypes but absent in parent genotypes, and)
(iii) a third restriction fragment length polymorphism band of about 2.8 kb length which is present in CMS genotypes but absent in parent genotypes.

2. A plant cell as claimed in claim 1, wherein the plant cell is part of the plant selected from *Brassica juncea, Brassica napus, Brassica carinata, Brassica oleracea, Brassica nigra* and *Brassica campestris*.

3. A male sterile *Brassica juncea* plant comprising, in its cytoplasm, a mitochondrial DNA exhibiting the following restriction fragment length polymorphism (RFLP) pattern under hybridization conditions:

A) a first RFLP pattern, such that when the mitochondrial DNA is digested with EcoRI as restriction enzyme and hybridized to cosmid clone pCos$^{13}$ (MTCC 5242) containing *B. oxyrrhina* mitochondrial DNA as probe, the pattern comprises:
(i) a first restriction fragment length polymorphism band of about 4.0 kb length which is present in CMS genotypes but absent in parent genotypes,
(ii) a second restriction fragment length polymorphism band of about 3.4 kb length which is present in parent genotypes but absent from CMS genotypes,
(iii) a third restriction fragment length polymorphism band of about 2.5 kb length which is present in CMS genotypes but absent in parent genotypes, and
(iv) a fourth restriction fragment length polymorphism band of about 0.7 kb length which is present in CMS genotypes but absent in parent genotypes;

B) a second RFLP pattern, such that when the mitochondrial DNA is digested with EcoRI as restriction enzyme and hybridized to cosmid clone pCos$^{17}$ (MTCC 5243) containing *B. oxyrrhina* mitochondrial DNA as probe, the pattern comprises:
(i) a first restriction fragment length polymorphism band of about 3.5 kb length which is present in parent genotypes but absent from CMS genotypes, and
(ii) a second restriction fragment length polymorphism band of about 1.7 kb length which is present in CMS genotypes but absent in parent genotypes; and C) a third RFLP pattern, such that when the mitochondrial DNA is digested with EcoRI as restriction enzyme and hybridized to cosmid clone pCos$^{42}$ (MTCC 5244) containing *B. oxyrrhina* mitochondrial DNA as probe, the pattern comprises:
(i) a first restriction fragment length polymorphism band of about 4.5 kb length which is present in CMS genotypes but absent in parent genotypes,
(ii) a second restriction fragment length polymorphism band of about 3.0 kb length which is present in CMS genotypes but absent in parent genotypes, and
(iii) a third restriction fragment length polymorphism band of about 2.8 kb length which is present in CMS genotypes but absent in parent genotypes.

4. A male sterile *Brassica juncea* plant as claimed in claim 3 wherein the microspores exhibit degeneration after tetrad stage.

5. The cell of a plant as claimed in claim 1, wherein:
the first RFLP pattern is the RFLP pattern of FIG. 2 (lanes 1 to 14) and FIG. 3 (lanes 1 to 4);
the second RFLP pattern is the RFLP pattern of FIG. 4 (lanes 1 to 14) and FIG. 5 (lanes 1 to 4); and
the third RFLP pattern is the RFLP pattern of FIG. 6 (lanes 1 to 14) and FIG. 7 (lanes 1 to 4).

6. The plant as claimed in claim 3, wherein:
the first RFLP pattern is the RFLP pattern of FIG. 2 (lanes 1 to 14) and FIG. 3 (lanes 1 to 4);
the second RFLP pattern is the RFLP pattern of FIG. 4 (lanes 1 to 14) and FIG. 5 (lanes 1 to 4); and
the third RFLP pattern is the RFLP pattern of FIG. 6 (lanes 1 to 14) and FIG. 7 (lanes 1 to 4).

\* \* \* \* \*